United States Patent [19]

Inagaki

[11] Patent Number: 4,969,866
[45] Date of Patent: Nov. 13, 1990

[54] APPARATUS FOR DRIVING A MEDICAL APPLIANCE

[75] Inventor: Yoshitaka Inagaki, Aichi, Japan

[73] Assignee: Aisin Seiki Kabushiki Kaisha, Aichi, Japan

[21] Appl. No.: 325,611

[22] Filed: Mar. 16, 1989

[30] Foreign Application Priority Data

Mar. 16, 1988 [JP] Japan .................................. 63-062934

[51] Int. Cl.$^5$ ............................................ A61N 1/362
[52] U.S. Cl. ...................................................... 600/18
[58] Field of Search ............................... 600/16, 17, 18

[56] References Cited

U.S. PATENT DOCUMENTS

| | | | |
|---|---|---|---|
| 3,266,487 | 8/1966 | Watkins et al. ....................... | 600/18 |
| 4,546,760 | 10/1985 | Suzuki et al. ......................... | 600/16 |
| 4,583,525 | 4/1986 | Suzuki et al. ......................... | 600/16 |
| 4,787,368 | 11/1988 | Kaseyama ............................. | 600/18 |
| 4,796,606 | 1/1989 | Mushika ................................ | 600/18 |
| 4,832,005 | 5/1989 | Takamiya et al. .................... | 600/18 |

Primary Examiner—Max Hindenburg
Assistant Examiner—S. Getzow
Attorney, Agent, or Firm—Sughrue, Mion, Zinn, Macpeak & Seas

[57] ABSTRACT

An apparatus for driving a medical appliance has a sensor for sensing a driving pressure which is an output pressure of the apparatus. The apparatus measures the rising and falling characteristics of the driving pressure by signals from the sensor. The apparatus adjusts the pressures in accordance with the rising and falling characteristics.

3 Claims, 6 Drawing Sheets

APPARATUS FOR DRIVING A MEDICAL APPLIANCE

BACKGROUND OF THE INVENTION

The present invention relates to an apparatus for driving a medical appliance such as an artificial heart or balloon pump in the main artery, more particularly to a fluid driving apparatus for regularly changing the fluid pressure.

A conventional driving apparatus for driving a medical appliance is shown in Japanese Kokai application No. 58(1983)-169460. When driving a medical pump such as an artificial heart pump, a positive pressure and a negative pressure are applied to a driving portion of the heart pump periodically in accordance with the pulsation of a natural heart so that the heart pump assists blood circulation. In order to drive a medical appliance in this way, the driving apparatus has a positive pressure generating device which generates a constant positive pressure, a negative pressure generating device which generates a constant negative pressure and a pressure changing device which changes the positive and negative pressures from the positive and negative pressure generating devices periodically. It is required for an artificial heart pump to change pressures quickly, from positive pressure to negative pressure and from negative pressure to positive pressure. Thus conventional driving apparatuses are designed to keep generating pressures as constant as possible. Generally, a positive pressure from the positive pressure generating device goes down when the positive pressure is applied to the heart pump and a negative pressure from negative pressure generating device goes down when the negative pressure is applied to the heart pump. To prevent these pressure drops, the positive and negative pressure generating devices are provided with accumulators for accumulating pressure reserves. Though accumulators may prevent such pressure drops, it is necessary to provide fairly big accumulators to prevent the pressure drops. As a result, the driving apparatus becomes extremely large and hard to move.

SUMMARY OF THE INVENTION

Accordingly, one of the objects of the present invention is to produce a driving apparatus for medical appliances to obviate the above drawbacks.

Another object of the present invention is to prevent pressure drops at the changing of pressures.

A further object of the present invention is to prevent pressure drops when a driving condition such as the volume of a heart pump is changed.

To achieve the above objects and in accordance with the principles of the invention as embodied and broadly described herein, an apparatus for driving a medical appliance has a positive pressure source, a positive pressure accumulator for accumulating said positive pressure, a positive pressure regulating means having an input port connected to said positive pressure source and an output port connected to said positive pressure accumulator, a negative pressure source, a negative pressure accumulator for accumulating said negative pressure, a negative pressure regulating means having an input port connected to said negative pressure source and an output port connected to said negative pressure accumulator, a negative pressure sensor for sensing pressure in said negative pressure accumulator connecting means for connecting said accumulators to a driving chamber of a medical appliance, means for changing pressures of said positive and negative pressure accumulators for applying a pressure to said connecting means, a driving pressure sensor for sensing pressure between said means for changing pressures and said driving chamber, control means for controlling said positive and negative pressure regulating means in accordance with pressures sensed by said positive and negative pressure sensors for setting pressures depending on which pressure is applied by said means for changing pressure and controlling said positive and negative pressure regulating means by measuring one of a rising or a dropping characteristic in accordance with the pressure sensed by said driving pressure sensor.

For example, the load to a positive pressure regulating device is small when a negative pressure is applied to a medical pump. However, the load is big when a positive pressure is applied. Therefore, if pressure regulating is controlled by comparing a sensed driving pressure with a set pressure, the response of regulation may be delayed. In order to prevent this delay, the system has two set pressures and controls a set pressure in accordance with loads. When a load is small, the pressure is set to a predetermined driving pressure and when a load is big, the pressure is set to an adjusting pressure which is bigger than the driving pressure. Japanese Kokai application No. 61(1986)-12900 shows a basic system for using two set pressures. However, in this system, it is important to decide a set pressure appropriately. If the adjusting pressure is set too small, effects of preventing pressure drops is not good when a load becomes big. On the contrary, if the adjusting pressure is too high, the pressure is too high when the load becomes large. There is also a need to adjust the adjusting pressure when a load on a pressure regulating device changes, i.e., the volume of a heart pump changes.

In accordance with the above mentioned apparatus of this invention, a control means measures a pressure dropping characteristic when a positive pressure is applied and a pressure rising characteristic when a negative pressure is applied and adjusts the adjusting pressures. Thus an apparatus according to this invention controls adjusting pressures automatically.

BRIEF DESCRIPTION OF THE DRAWINGS

For as full understanding of the true scope of the invention, the following detailed description should be read in conjunction with the drawings, wherein.

DETAILED DESCRIPTION OF THE PREFERRED EMBODIMENTS

In the following, preferred embodiments of the present invention will be described with reference to the drawings.

Figure 2:
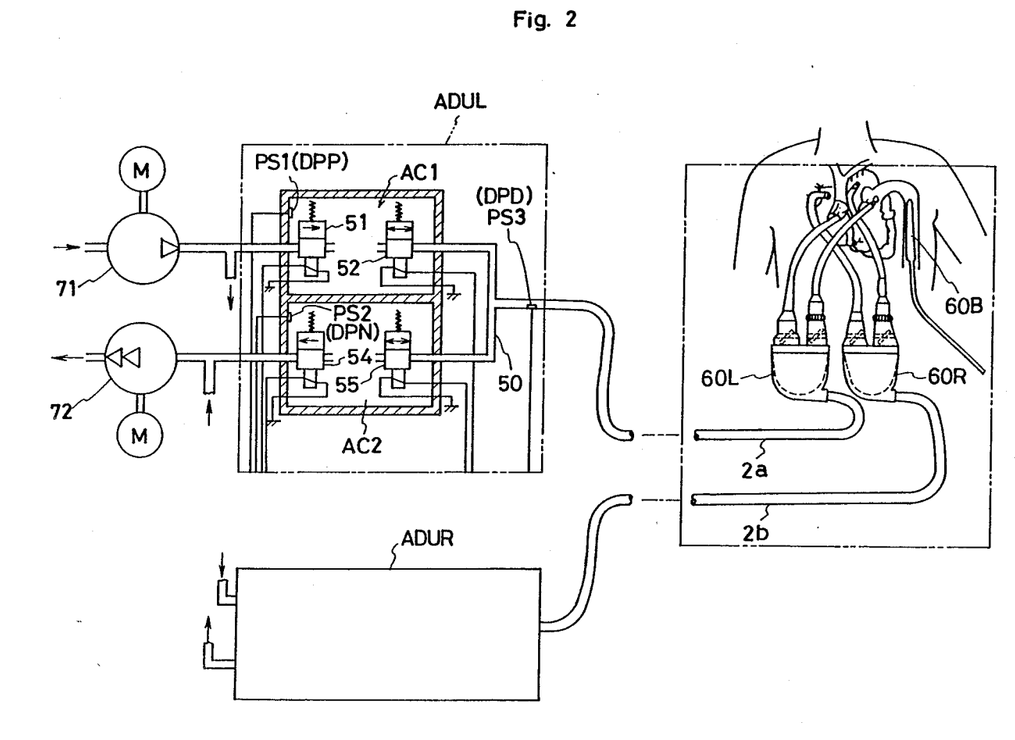
FIG. 2 is a block diagram schematically showing a driving apparatus of the present invention.

FIG. 2 illustrates one embodiment of a driving apparatus of the present invention. A pair of artificial hearts are designated at 60L and 60R. This type of artificial heart is called an assistance artificial heart because it is used for assistance of a natural heart or temporarily used as a substitute heart. Each artificial heart has a blood chamber and a driving chamber separated by a flexible diaphragm and has valves at the input and output of the blood chamber. The diaphragm is driven periodically by applying a pulsatile fluid to the driving chamber so that the blood is pumped from the input to the output of the blood chamber. Pressure supply tubes 2a and 2b are connected to the driven chambers of the artificial hearts 60L and 60R, respectively. In this embodiment, the artificial heart is driven by air pressure. This embodiment has two air pressure control units ADUL and ADUR in order to drive the two artificial hearts 60L and 60R at the same time. These two control units ADUL and ADUR are identical and accordingly, the control unit ADUL will be explained.

The air pressure control unit ADUL has four electric valves 51, 52, 54 and 55. The electric valves 51 and 52 are positioned in the accumulator AC1 and the electric valves 54 and 55 are positioned in the accumulator AC2. The electric valves 51 and 54 regulate the air pressures in the accumulators AC1 and AC2. An inlet port of the electric valve 51 is connected to a compressor 71 and an outlet port is connected to the accumulator AC1. An inlet port of the electric valve 54 is connected to a vacuum pump 72 and an outlet port is connected to the accumulator AC2. Inlet ports of the electric valves 52 and 55 are connected to the accumulators AC1 and AC2, respectively. The outlet ports of the electric valves 52 and 55 are connected by a pipe 50 which is connected to a tube 2a of the artificial heart 60L.

Pressure sensors PS1 and PS2 are placed in the accumulators AC1 and AC2 in order to detect pressures DPP and DPN. A pressure sensor PS3 is placed in the pipe 50 to detect a driving pressure DPD.

Figure 3:
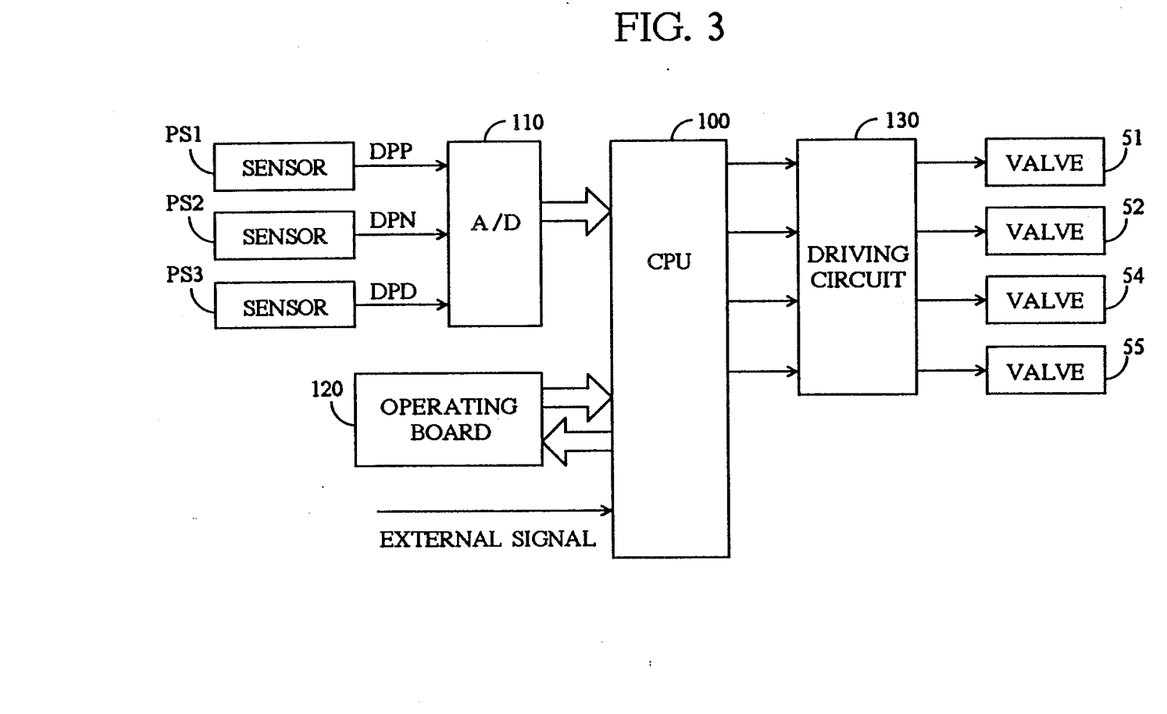
FIG. 3 is a circuit diagram showing the circuitry of the pressure controlling unit ADUL.

FIG. 3 shows an electrical circuit for controlling the air pressure control unit ADUL shown in FIG. 2. The air control unit ADUR is controlled by an electrical circuit identical to that shown in FIG. 3.

Referring to FIG. 3, the circuit has a microprocessor 100. I/O ports of the microprocessor 100 are connected to an A/D conversion circuit 110, operating board 120 and driver circuit 130. The pressure sensors PS1, PS2 and PS3 output analog electric signals to the A/D conversion circuit 110. The A/D conversion circuit 110 converts these signals into digital signals for supply to the microprocessor 100. The operating board 120 has key switches to input driving parameters and a display (not shown) to show the parameters. The parameters include set pressures of positive and negative pressures, duration of applying a positive pressure, duration of applying a negative pressure, heart beat period, etc. The four electric valves 51, 52, 54 and 55 are connected to the microprocessor 100 through the driving circuit 130.

Figure 4A:
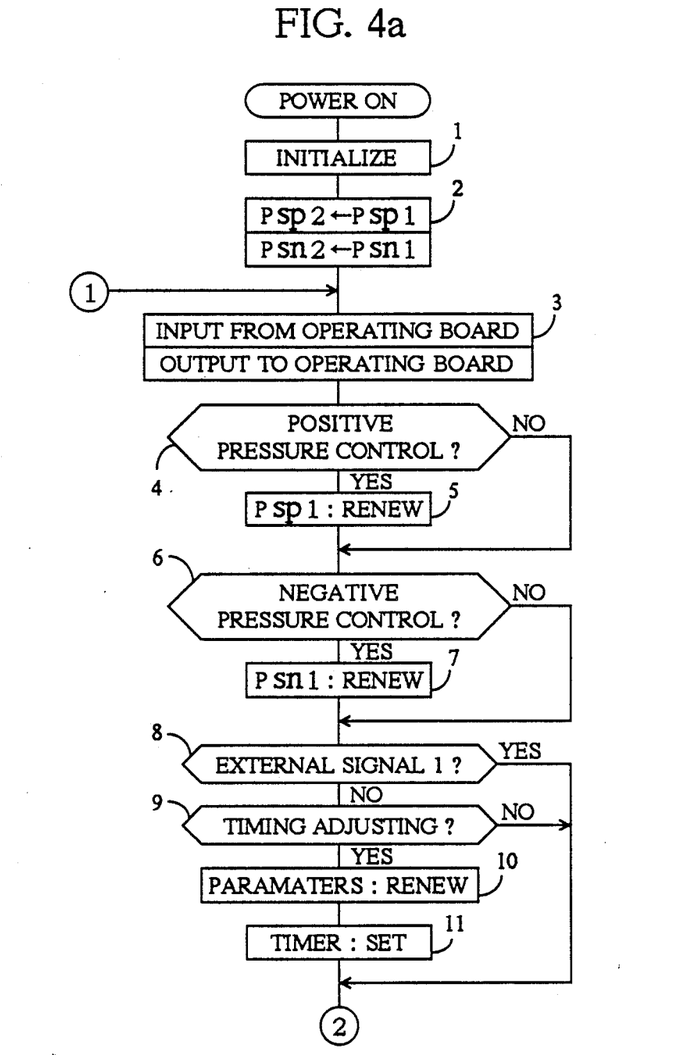
FIGS. 4a, 4b and 4c are flow charts showing the operation of the processor 100.
Figure 4B:
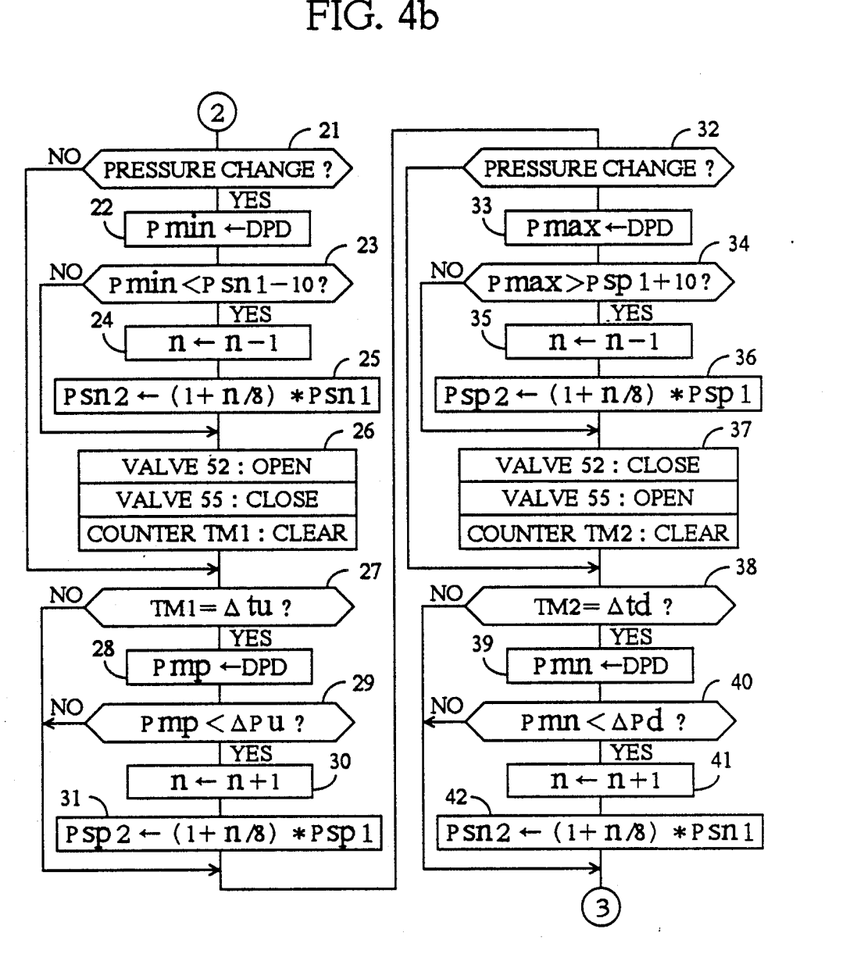
Figure 4C:
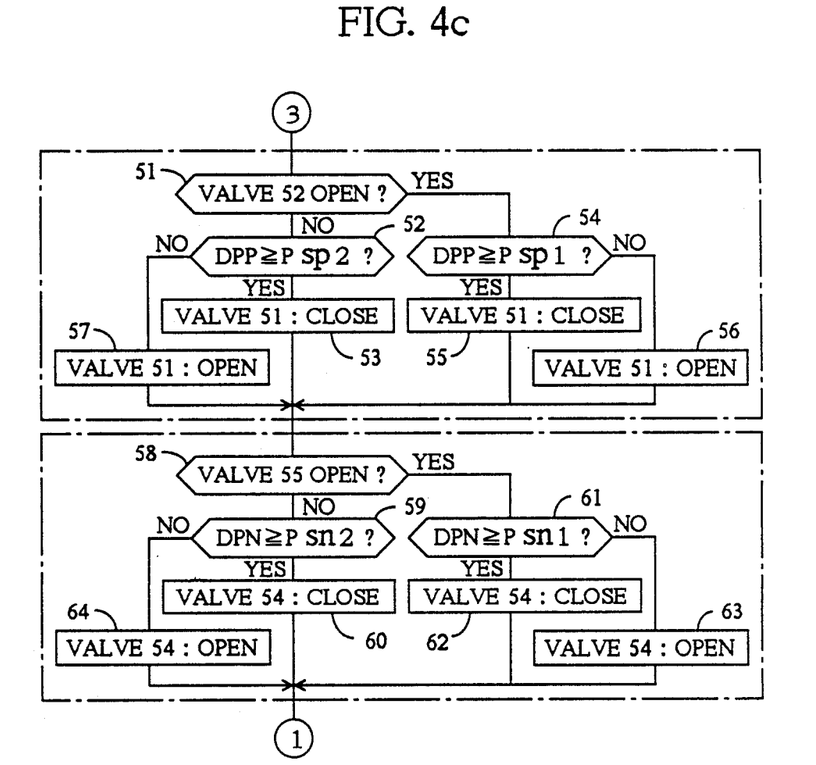

FIGS. 4a, 4b and 4c are flowcharts showing an operation of the microprocessor 100. Referring to FIG. 4a, when the power is turned on, the parameters are initialized to clear memory and output signals and set the predetermined parameters in the memory as initial values. A positive set pressure for the positive pressure control is stored in a positive set pressure register Psp1 and a negative set pressure for the negative pressure control is stored in a negative set pressure register Psn1. A value of the positive set pressure register Psp1 is used as a target pressure for positive pressure control when the electric valve 52 is closed and a value of the negative set pressure register Psn1 is used as a target pressure for negative pressure control when the electric valve 55 is closed. In step 2 after initializing, the values of set pressure registers Psp1 and Psn1 are stored in adjusting pressure registers Psp2 and Psn2, respectively. A value of the positive adjusting pressure register Psp2 is used for a target pressure for positive pressure control when the electric valve 52 is opened and a value of the negative adjusting pressure register Psn2 is used for a target pressure for negative pressure control when the electric valve 55 is opened. In step 3, the system reads keys of the operation board 120 and displays parameters. When a switch which indicates a change of a positive set pressure is operated, the system goes to steps 4 and 5 to renew the value of the positive set pressure register Psp1. When a switch which indicates a change of a negative set pressure is operated, the system goes to steps 6 and 7 to renew the value of the negative set pressure register Psn1.

When the system does not use an external timing signal, the system goes to steps 8 and 9. If the switches on the operation board 120 indicate durations of applying positive and negative pressures or a pumping rate, the system goes to steps 10 and 11. Parameters are changed in accordance with such indication and a timer is set to determine a pumping timing for changing positive/negative pressures.

Figure 1:
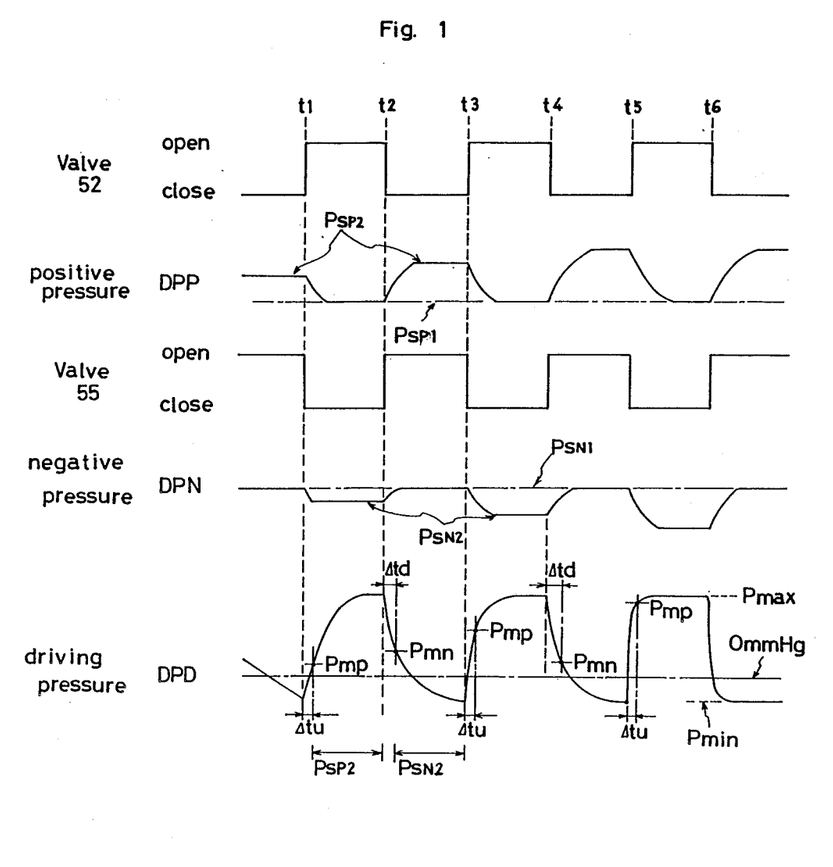
FIG. 1 is a timing chart showing status of valves and changes of pressures of a driving apparatus of the present invention as shown in FIG. 2.

Referring to FIG. 4b, in step 21 a decision is made whether the timing for changing positive/negative pressures is in accordance with an internal timer or an external signal, that is, to decide whether the timing is equal to times t1, t2 or t3 as shown in FIG. 1. If the timing is equal to the times, the system goes to step 22. In step 22, a signal DPD from the pressure sensor PS3 is read and the value is set as Pmin as the lowest pressure (maximum negative pressure). In step 23, the detected lowest pressure is checked whether it is in an appropriate range. If pressure Pmin is smaller than the pressure Psn1−10 mmHg, the pressure is too small (negative pressure is too big). Then the system executes steps 24 and 25 to renew the value of the negative adjusting pressure register Psn2. If not, the value of the register Psn2 is kept the same. In step 26, the electric valve 52 is opened, the electric valve 55 is closed and the counter TM1 is cleared. By these steps, the pressure applied to the artificial heart is changed from negative pressure into positive pressure. The counter TM1 counts up every predetermined short time period so that the counter TM1 counts time after a pressure change.

In steps 27 to 31, the system measures the rising characteristic of a driving pressure changed from negative pressure to positive pressure and renews the value of the positive adjusting pressure register Psp2 in accordance with the measured rising characteristic. In step 27, the system compares a value of the counter TM1 with a predetermined time $\Delta$ tu. If the value is the same as $\Delta$ tu, that is, the value si timings t1+$\Delta$ tu, t3 +$\Delta$ tu, or t5+$\Delta$ tu, the system goes to step 28. In step 28, a signal DPD from the pressure sensor PS3 is read and the value is set as a pressure Pmp. In step 29, a sensed pressure Pmp is compared with reference pressure $\Delta$ Pu. If pressure Pmp is smaller than $\Delta$ Pu, a decision is made that a pressure rising is too late. In step 30, a value in a register n is incremented and in step 31 a value in the positive adjusting pressure is renewed in accordance with a positive set pressure register Psp1 and a register n. Therefore, it a pressure rising is delayed, the value of the adjusting pressure register Psp2 is increased though a value of the set pressure register Psp1 is constant. If a pressure Pmp is the same or greater than pressure Δ Pu, a renewal of the register Psp2 is not done.

In step 32, a decision is made whether it is time to change pressures from positive into negative in accordance with the internal timer or the external signal, that is, to decide whether it is times t2, t4 or t6 as shown in FIG. 1. If the timings are the same, then the system goes to step 33. In step 33, a signal DPD from the pressure sensor PS3 is read and the value is set as Pmax as the highest pressure. In step 34, a detected highest pressure is checked to determine if it is in an appropriate range. If pressure Pmax is greater than the pressure Psp1+10 mmHg, the pressure is too high. Then the system executed steps 35 and 36 to renew the value of the positive adjusting pressure register Psp2. Therefore, if pressure Pmax becomes too high, the value of the adjusting pressure register Psp2 is decreased though the value of the set pressure register Psp1 is constant.

In step 37, the electric valve 52 is closed, the electric valve 55 is opened and the counter TM2 is cleared. By these steps the pressure applied to the artificial heart is changed from positive pressure to negative pressure. The counter TM2 counts up every predetermined short time period so that the counter TM2 counts time after a pressure change. In steps 38 to 42, the system measures the dropping characteristic of a driving pressure changed from positive pressure to negative pressure and renews the value of the negative adjusting pressure register Psn2 in accordance with a measured pressure drop characteristic. In step 38, the system compares a value of the counter TM2 with a predetermined time Δ td. If the value is as same as Δ td, that is, the value is time t2+Δ td, t4+Δ td or t6+Δ td, the system goes to step 39. In step 39, a signal DPD from the pressure sensor PS3 is read and the value is set as a negative pressure Pmn. In step 39, a sensed pressure Pmn is compared with a reference pressure Δ Pd. If pressure Pmn is greater than Δ Pd, a decision is made that the pressure drop is too late. In step 41, a value in the register n is incremented and in step 42 a value in the negative adjusting pressure is renewed in accordance with a negative set pressure register Psn1 and the register n. Therefore, if a pressure drop is delayed, a value of the adjusting pressure register Psn2 is increased though a value of the set pressure register Psn1 is constant. If a pressure Pmn is the same or smaller than pressure Δ Pd, a renewal of the register Psn2 is not done.

Referring to FIG. 4c, this shows the pressure control of accumulators AC1 and AC2 in accordance with the values of set pressure registers Psp1 and Psn1 and adjusting pressure registers Psp2 and Psn2.

A positive pressure control, that is, a pressure control of the accumulator AC1 will be explained. First, the system checks if the electric valve 52 is closed or opened in step 51. If the electric valve 52 is open, a sensed pressure is compared with a value of the set pressure register Psp1. If the electric valve 52 is closed, a sensed pressure is compared with a value of the adjusting register Psp2. Thus a target pressure of the positive pressure control when a negative pressure is applied to the artificial heart is bigger than that when a positive pressure is applied.

If the electric valve 52 is opened, a sensed pressure DPP from the pressure sensor PS1 is compared with a value of the register Psp1. If the sensed pressure DPP is the same or greater than the set pressure Psp1, the electric valve 51 is closed. If not, the electric valve 51 is opened.

If the electric valve 52 is closed, a sensed pressure DPP is compared with a value of the register Psp2. If the sensed pressure DPP is the same or greater than the set pressure Psp2, the electric valve 51 is closed. If not, the electric valve 51 is opened.

A negative pressure control, that is, a pressure control of the accumulator AC2 will be explained. First, the system checks if the electric valve 55 is closed or opened in step 58. If the electric valve 55 is opened, a sensed pressure is compared with a value of the set pressure register Psn1. If the electric valve 55 is closed, a sensed pressure is compared with a value of the adjusting register Psn2. Thus a target pressure of the negative pressure control when a positive pressure is applied to the artificial heart is bigger than that when a negative pressure is applied.

If the electric valve 55 is opened, a sensed pressure DPN from the pressure sensor PS2 is compared with a value of the register Psn1. If the sensed pressure DPN is the same or smaller than the set pressure Psn1, the electric valve 54 is closed. If not, the electric valve 54 is opened.

If the electric valve 55 is closed, a sensed pressure DPN is compared with a value of the register Psn2. If the sensed pressure DPN is the same or smaller than the set pressure Psn2, the electric valve 54 is closed. If not, the electric valve 54 is opened.

The aforementioned operation (after step 3) is executed periodically in a short time so that a pressure of the accumulator AC1 is kept constant at the pressure of registers PSp1 or Psp2 and a pressure of the accumulator AC2 is kept constant at the pressure of registers Psn1 or Psn2.

At the beginning of the control, values of the set pressure registers Psp2 and Psn2 are set at the same value as the set pressure registers Psp1 and Psn1. Parameters show changes as shown in FIG. 1, a driving pressure DPD changes with delayed rising or dropping characteristics because a pressure drop (DPP) of the accumulator AC1 when the electric valve 52 is opened and a pressure drop (DPN) of the accumulator AC2 when the electric valve 55 is opened. However, as time passes, the pressure supply ability of the accumulator AC1 when the electric valve 52 is opened and the pressure supply ability of the accumulator AC2 when the electric valve 55 is opened are increased, because values of the registers PSp2 and Psn2 are increased gradually. Thus the driving pressure changes with sharp pressure drop and rise.

If values of the registers Psp2 and Psn2 are too big, a higher pressure than target pressure (values of the registers Psp2 and Psn2) may be applied to the artificial heart. However, in this embodiment the maximum pressure Psp2 and Psn2 are feedbacks to the register Psp2 and Psn2. Therefore, the driving pressure DPD is kept at the best condition.

In this embodiment, a compressor is used for the positive pressure source and a vacuum pump is used for the negative pressure source, however it may be constructed by single compressor as shown in Japanese Kokai Application No. 61(1986)-129500.

The invention has been described in an illustrative manner, and it is to be understood that the terminology which has been used is intended to be in the nature of words of description rather than of limitation.

Obviously, many modifications and variations of the present invention are possible in light of the above teachings. It is therefore, to be understood that within the scope of the appended claims, the invention may be practice otherwise than as specifically described.

What is claimed is:

1. An apparatus for driving a medical appliance comprising:
    a positive pressure source for supplying a positive pressure,
    a positive pressure accumulator for accumulating said positive pressure,
    a positive pressure regulating means having an input port connected to said positive pressure source and an output port connected to said positive pressure accumulator,
    a positive pressure sensor for sensing a pressure of said positive pressure accumulator,
    a negative pressure source for supplying a negative pressure,
    a negative pressure accumulator for accumulating said negative pressure,
    a negative pressure regulating means having an input port connected to said negative pressure source and an output port connected to said negative pressure accumulator,
    a negative pressure sensor for sensing a pressure of said negative pressure accumulator,
    connecting means for connecting an output of each accumulator to a driving chamber of a medical appliance,
    means for changing pressures of said positive and negative pressure accumulators for applying a pressure to said connecting means,
    a driving pressure sensor for sensing a pressure between said means for changing pressures and said driving chamber, and
    control means for controlling said positive and negative pressure regulating means in accordance with pressures sensed by said positive and negative pressure sensors, for setting pressures depending on which pressure is applied by said means for changing pressures and controlling said positive and negative pressure regulating means by measuring a changing pressure characteristic in accordance with a pressure sensed by said driving pressure sensor, said control means sets a set pressure of said positive pressure regulating means with a driving positive pressure and sets a set pressure of said negative pressure regulating means with an adjusting positive pressure when said means for changing pressure applies said driving positive pressure, sets a set pressure of said positive pressure regulating means with an adjusting positive pressure and sets a set pressure of said negative pressure regulating means with a driving negative pressure when said means for changing pressure applies said driving negative pressure, adjusts said adjusting positive pressure in accordance with a pressure sensed by said driving pressure sensor a predetermined time after said means for changing pressure applies said driving positive pressure, and adjusts said adjusting negative pressure in accordance with a pressure sensed by said driving pressure sensor a predetermined time after said means for changing pressure applies said driving negative pressure.

2. An apparatus for driving a medical appliance comprising:
    a positive pressure source for supplying a positive pressure,
    a positive pressure accumulator for accumulating said positive pressure,
    a positive pressure regulating means having an input port connected to said positive pressure source and an output port connected to said positive pressure accumulator,
    a positive pressure sensor for sensing a pressure of said positive pressure accumulator,
    a negative pressure source for supplying a negative pressure,
    a negative pressure accumulator for accumulating said negative pressure,
    a negative pressure regulating means having an input port connected to said negative pressure source and an output port connected to said negative pressure accumulator,
    a negative pressure sensor for sensing a pressure of said negative pressure accumulator,
    connecting means for connecting an output of each accumulator to a driving chamber of a medical appliance,
    means for changing pressures of said positive and negative pressure accumulators for applying a pressure to said connecting means,
    a driving pressure sensor for sensing a pressure between said means for changing pressures and said driving chamber, and
    control means for controlling said positive and negative pressure regulating means in accordance with pressures sensed by said positive and negative pressure sensors, for setting pressures depending on which pressure is applied by said means for changing pressures and controlling said positive and negative pressure regulating means by measuring a changing pressure characteristic in accordance with a pressure sensed by said driving pressure sensor, said control means sets a set pressure of said positive pressure regulating means with a driving positive pressure and sets a set pressure of said negative pressure regulating means with an adjusting positive pressure when said means for changing pressure applies said driving positive pressure, sets a set pressure of said positive pressure regulating means with an adjusting positive pressure and sets a set pressure of said negative pressure regulating means with a driving negative pressure when said means for changing pressure applies said driving negative pressure, and adjusts said adjusting positive pressure in accordance with a pressure sensed by said driving pressure sensor a predetermined time after said means for changing pressure applies said driving positive pressure.

3. An apparatus for driving a medical appliance comprising:
    a positive pressure source for supplying a positive pressure,
    a positive pressure accumulator for accumulating said positive pressure,
    a positive pressure regulating means having an input port connected to said positive pressure source and an output port connected to said positive pressure accumulator,
    a positive pressure sensor for sensing a pressure of said positive pressure accumulator,
    a negative pressure source for supplying a negative pressure,
    a negative pressure accumulator for accumulating said negative pressure, a negative pressure regulating means having an input port connected to said negative pressure source and an output port connected to said negative pressure accumulator, a negative pressure sensor for sensing a pressure of said negative pressure accumulator, connecting means for connecting an output of each accumulator to a driving chamber of a medical appliance, means for changing pressures of said positive and negative pressure accumulators for applying a pressure to said connecting means, a driving pressure sensor for sensing a pressure between said means for changing pressures and said driving chamber, and control means for controlling said positive and negative pressure regulating means in accordance with pressures sensed by said positive and negative pressure sensors, for setting pressures depending on which pressure is applied by said means for changing pressures and controlling said positive and negative pressure regulating means by measuring a changing pressure characteristic in accordance with a pressure sensed by said driving pressure sensor, said control means sets a set pressure of said positive pressure regulating means with a driving positive pressure and sets a set pressure of said negative pressure regulating means with an adjusting positive pressure when said means for changing pressure applies said driving positive pressure, sets a set pressure of said positive pressure regulating means with an adjusting positive pressure and sets a set pressure of said negative pressure regulating means with a driving negative pressure when said means for changing pressure applies said driving negative pressure, and adjusts said adjusting negative pressure in accordance with a pressure sensed by said driving pressure sensor a predetermined time after said means for changing pressure applies said driving negative pressure.

* * * * *